(12) United States Patent
Heilman et al.

(10) Patent No.: US 8,168,838 B2
(45) Date of Patent: May 1, 2012

(54) HYDROCARBON COMPOSITIONS USEFUL AS LUBRICANTS

(75) Inventors: William J Heilman, Houston, TX (US); Yajnanarayana Halmuthur Jois, Katy, TX (US); Abraham Robert De Kraker, Sugar Land, TX (US); Wei Song, Houston, TX (US)

(73) Assignee: Shell Oil Company, Houston, TX (US)

( * ) Notice: Subject to any disclaimer, the term of this patent is extended or adjusted under 35 U.S.C. 154(b) by 166 days.

(21) Appl. No.: 12/689,709

(22) Filed: Jan. 19, 2010

(65) Prior Publication Data

US 2011/0178348 A1 Jul. 21, 2011

Related U.S. Application Data

(60) Provisional application No. 61/146,132, filed on Jan. 21, 2009.

(51) Int. Cl.
*C10M 105/04* (2006.01)
*C07C 9/22* (2006.01)

(52) U.S. Cl. .............. 585/18; 585/16; 585/17; 585/255; 585/510; 508/110

(58) Field of Classification Search .................. 585/16, 585/17, 18, 255
See application file for complete search history.

(56) References Cited

U.S. PATENT DOCUMENTS

| | | | |
|---|---|---|---|
| 4,045,507 A | 8/1977 | Cupples et al. | 260/683.15 |
| 4,045,508 A | 8/1977 | Cupples et al. | 260/683.15 |
| 5,015,795 A * | 5/1991 | Pelrine | 585/530 |
| 5,284,988 A | 2/1994 | Schaerfl et al. | 585/525 |
| 5,382,739 A * | 1/1995 | Atkins et al. | 585/530 |
| 5,498,815 A | 3/1996 | Schaerfl et al. | 585/512 |
| 5,688,887 A | 11/1997 | Bagheri et al. | 526/348.7 |
| 6,245,719 B1 | 6/2001 | Kobori | 508/110 |
| 6,586,646 B1 | 7/2003 | Heilman et al. | 585/12 |
| 6,703,356 B1 * | 3/2004 | Wu | 508/591 |
| 7,129,197 B2 | 10/2006 | Song et al. | 508/591 |
| 2009/0221775 A1 * | 9/2009 | Hagemeister et al. | 526/183 |

FOREIGN PATENT DOCUMENTS

| | | |
|---|---|---|
| EP | 0613886 | 9/1994 |
| EP | 0613887 | 9/1994 |
| WO | WO9010050 | 9/1990 |
| WO | WO2009073135 | 6/2009 |

OTHER PUBLICATIONS

Viscometric and Tribological Properties of New High Performance Synthetic Hydrocarbon Fluids, by B. L. Papke, W. J. Heilman, Y. H. Jois, A. R. De Kraker, L. M. Morrison, M. Pozebanchuk and W. Song, Shell Global Solutions (U.S.) Inc., Houston, TX.

* cited by examiner

*Primary Examiner* — Ellen McAvoy

(57) ABSTRACT

A process for the preparation of a synthetic predominantly single carbon number hydrocarbon fluid comprises the steps of: contacting an alpha olefin having a carbon number of 4 to 30 with a single site catalyst under conditions effective to produce reactive hydrocarbon oligomers that contain reactive double bonds and comprising predominantly dimers, trimers, and tetramers wherein at least 10 weight percent of such reactive hydrocarbon oligomers at least one of trimers and tetramers; separating at least one of said trimers and tetramers in said reactive hydrocarbon oligomers; dimerizing said separated one of said trimers tetramers by contacting said separated one of said trimers or tetramers with a dimerization catalyst thereby producing an unsaturated synthetic hydrocarbon fluid; and contacting said unsaturated synthetic hydrocarbon fluid with hydrogen in the presence of a hydrogenation catalyst thereby producing a synthetic hydrocarbon fluid having predominantly single carbon number.

20 Claims, 1 Drawing Sheet

HYDROCARBON COMPOSITIONS USEFUL AS LUBRICANTS

RELATED CASES

The present case claims benefit of U.S. Application Ser. No. 61/146,132, filed on 21 Jan. 2009, which is incorporated herein by reference.

FIELD OF THE INVENTION

The present invention relates to a hydrocarbon composition useful as a lubricant and the process for the production of such hydrocarbon composition.

BACKGROUND OF THE INVENTION

The commercial polyalphaolefins (PAO) typically are dimers, trimers and tetramers of 1-octene, 1-decene and 1-dodecene and are typically made by a two-stage process described in U.S. Pat. No. 4,045,507. The PAO oligomerization process is carried out using boron trifluoride with a complex-forming co-catalyst. The multistage process can include two continuous stirred tank reactors in series. Generally 1-decene or 1-dodecene and the co-catalyst usually an alcohol such as 1-butanol are added to the first reactor. Boron trifluoride gas is maintained over the two reaction vessels to form the boron trifluoride-alcohol catalyst in the reactors.

The oligomer product prepared by such a two-stage process is a mixture of dimer, trimer, tetramer and a small amount of higher oligomers. The oligomers are hydrogenated and the primary products, trimer and tetramer, are distilled to make hydrocarbon products that have viscosities at 100° C. of 2 cSt, 4 cSt, 6 cSt and 8 cSt. The trimer is 4 cSt and the tetramer is 8 cSt. 6 cSt PAO is a mixture of trimer and tetramer that is readily available commercially.

Less used but also commercially available polyalpha olefins are 40 cSt and 100 cSt made by a different process.

Boron trifluoride combines in the first reactor with the co-catalyst that is commonly an alcohol to form a coordination compound that is catalytically active for the oligomerization reaction. These cationic catalysts are typically at 110° F. and are known to produce a significant amount of isomerization of the double bond in the alphaolefin before oligomerization, increasing the amount of branching on the hydrocarbon backbone. Isomerization branching also occurs on the hydrocarbon chains in the branches. Branching in the oligomers gives conventional PAO a broad boiling point distribution.

SUMMARY OF THE INVENTION

In accordance with one embodiment of the invention, there is provided a process for the preparation of a synthetic predominantly single carbon number hydrocarbon fluid comprising the steps of:
(a) contacting an alpha olefin having a carbon number of 6 to 30 with a single site catalyst under conditions effective to produce at least 10 weight percent of the combined trimer and tetramer based on total oligomer products thereby producing reactive hydrocarbon oligomers that contain reactive double bonds and comprising predominantly dimers, trimers, and tetramers wherein at least 10 weight percent of such reactive hydrocarbon oligomers are trimers and tetramers;
(b) separating at least one of said trimers and tetramers in said reactive hydrocarbon oligomers; and
(c) dimerizing at least one of said separated trimers or separated tetramers by contacting said at least one separated trimers or tetramers with a dimerization catalyst thereby producing an unsaturated synthetic hydrocarbon fluid;
(d) contacting said unsaturated synthetic hydrocarbon fluid with hydrogen in the presence of a hydrogenation catalyst thereby producing a synthetic hydrocarbon fluid having predominantly a single carbon number.

Further, a predominantly single carbon synthetic hydrocarbon fluid is provided having a carbon number of 60, a Noack volatility value of less than 1.5 weight percent, an average of about one quaternary carbon atom per molecule and a boiling point distribution at 10 weight percent distilled to 90 weight percent distilled within the range of 500° C. to 620° C.

Yet further, a predominantly single carbon synthetic hydrocarbon fluid is provided having a carbon number of 80, a Noack volatility value of less than 1.0 weight percent, an average of about one quaternary carbon atom per molecule and a boiling point distribution at 10 weight percent distilled to 90 weight percent distilled within the range of 500° C. to 690° C.

In another embodiment of the invention, synthetic hydrocarbon fluids useful for lubricating applications are provided that are predominantly single carbon number hydrocarbon having a narrow boiling point distribution.

BRIEF DESCRIPTION OF THE DRAWINGS

For a more complete understanding of the invention, reference is made to the accompanying Figures, wherein.

DETAILED DESCRIPTION OF THE INVENTION

Figure 1:
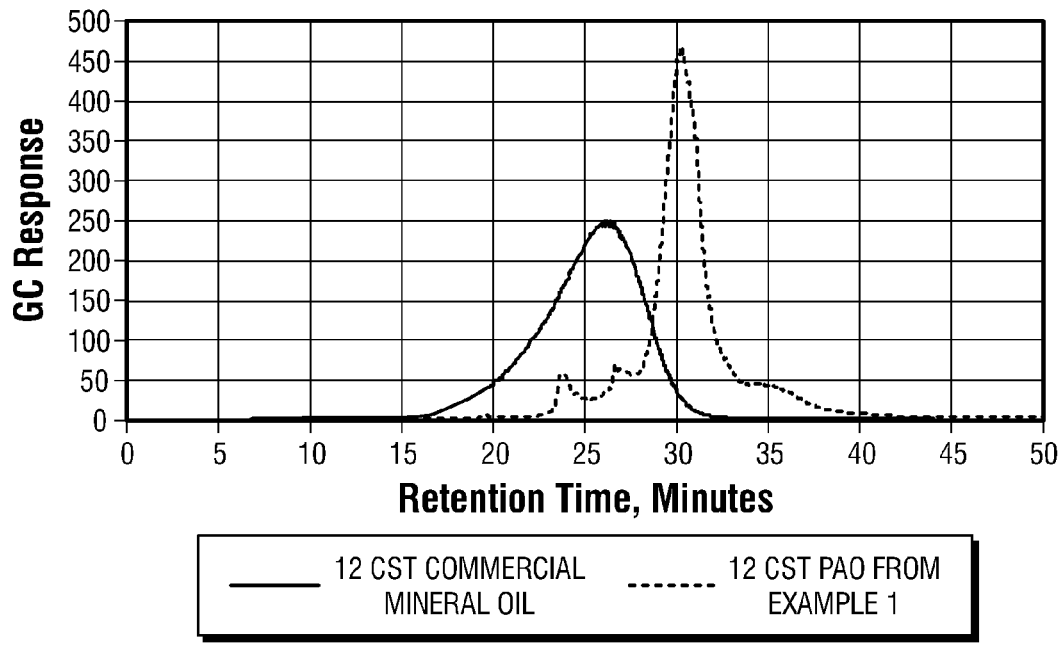
FIG. 1 is a plot of boiling point distributions of a commercial 12 cst mineral oil and PAO produced from 1-decene according to the invention from Example 1.

In one embodiment, the invention relates to the production of novel hydrocarbon oligomers. The hydrocarbon oligomers are produced by first reacting certain alphaolefins with a single site catalyst to produce reactive hydrocarbon oligomers (trimers, tetramers etc.) that contain reactive double bonds. The reactive hydrocarbon oligomers can be separated into single trimer and tetramer compounds. The separated reactive hydrocarbon oligomers are dimerized into predominantly single carbon number unsaturated synthetic fluids. The term "predominantly" means that such component is the major component in the composition, preferably 60% or greater, more preferably 80% or greater.

The synthetic fluids have branching that contains in the average about one quaternary carbon atom per molecule. After subsequent hydrogenation, the synthetic fluids contain a major amount of a component having the structure:

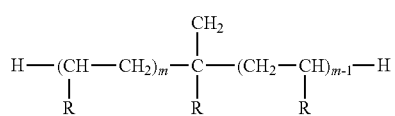

wherein m is an integer from 3 to 4 and R is an alkyl group having a carbon number from 2 to 28.

As one embodiment of the invention, for example, when a decene trimer is dimerized and subsequently hydrogenated, the synthetic fluid contains a predominantly single carbon synthetic hydrocarbon fluid comprising a major amount of a compound having the formula:

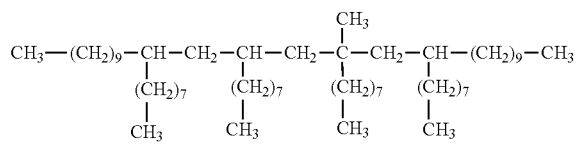

In an another embodiment of the invention, when a decene tetramer is dimerized and subsequently hydrogenated, the synthetic fluid contains a predominantly single carbon synthetic hydrocarbon fluid comprising a major amount of a compound having the formula:

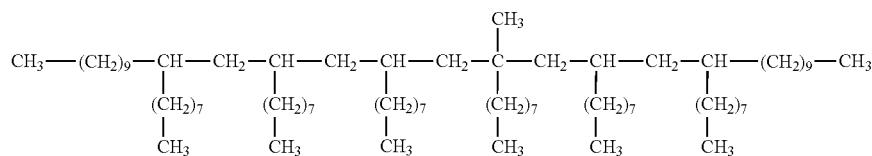

The synthetic predominantly single carbon number hydrocarbon fluid can be prepared by a process comprising:
(a) contacting an alpha olefin having a carbon number of 6 to 30 with a single site catalyst under conditions effective to produce at least 10 weight percent of the combined trimer and tetramer based on total oligomer products thereby producing reactive hydrocarbon oligomers that contain reactive double bonds and comprising predominantly dimers, trimers, and tetramers wherein at least 10 weight percent of such reactive hydrocarbon oligomers are trimers and tetramers;
(b) separating at least one of said trimers and tetramers in said reactive hydrocarbon oligomers; and
(c) dimerizing at least one of said separated trimers or separated tetramers by contacting said at least one separated trimers or tetramers with a dimerization catalyst thereby producing an unsaturated synthetic hydrocarbon fluid;
(d) contacting said unsaturated synthetic hydrocarbon fluid with hydrogen in the presence of a hydrogenation catalyst thereby producing a synthetic hydrocarbon fluid having predominantly single carbon number.

In one aspect of the present invention, the alphaolefins are allowed to react with a single site catalyst to produce reactive hydrocarbon oligomers (dimers, trimers, tetramers etc.) that contain reactive double bonds. For step (a), the single site catalyst useful for the invention can be, for example, organometallic complexes containing Zirconium, Titanium, Niobium, and Hafnium. Any catalyst which is capable of effecting oligomerization of the olefin monomer may be used in embodiments of the invention, preferably capable of minimizing the occurrence of isomerization of the alphaolefin monomer during reaction. Suitable catalysts include, but are not limited to, single site catalyst (both metallocene catalysts and constrained geometry catalyst), and variations therefrom. It should be understood that the term "catalyst" as used herein refers to a metal-containing compound which is used, along with an activating cocatalyst, to form a catalyst system. The catalyst, as used herein, is usually catalytically inactive in the absence of a cocatalyst or other activating technique. However, not all suitable catalyst are catalytically inactive without a cocatalyst and thus requires activation. Examples of useful catalysts are described in U.S. Pat. No. 7,129,197, which disclosure is hereby incorporated by reference. A preferred single site catalyst is a complex of bis(cyclopentadienyl)zirconium dichloride and an alkylaluminoxane. The reaction is carried out preferably at a temperature in the range of from about 0° C., more preferably from about 20° C., to preferably about 90° C., to more preferably about 60° C. The catalyst concentration is preferably in the range of 20 to 2000 micromoles per mole of olefin monomer, more preferably 100 to 400 micromoles per mole of olefin monomer, most preferably about 200 micromoles per mole of monomer. The cocatalyst concentration is preferably in the range of 10 to 1000 moles per mole of catalyst, more preferably 50 to 500 moles per mole of catalyst, most preferably about 100 moles per mole of catalyst.

The starting alpha olefins are commercially available from Shell Chemical LP, Chevron Phillips Chemical Company LLC, Sasol Limited, Idemitsu Kosan Co. Ltd., Mitsubishi Chemical Corporation and other manufactures. The alphaolefins can have carbon numbers from four to twenty plus and can be odd carbon numbered alphaolefins. Olefins that can be polymerized with a single site catalyst can be used. For example olefins having from 4 carbon atoms, preferably from 6, more preferably from 8 carbon atoms, to 30 carbon atoms, preferably to 14 carbon atoms, more preferably to 10 carbon atoms can be used as the starting material. Examples of the alpha olefins that can be used in the process of this invention are, 1-butene, 1-pentene, 1-hexene, 1-heptene, 1-octene, 1-nonene, 1-decene, 1-dodecene, 1-tetradecene, 1-hexadecene, 1-octadecene, 1-eicosene, 4-ethyl-1-pentene, 2-methyl-1-hexene, and 4-methyl-1-pentene.

The resulting reactive hydrocarbon oligomer mixture can conveniently be separated by distillation in order to obtain relatively pure trimer and tetramer fractions by distillation methods known in the art.

The separated reactive hydrocarbon oligomers are dimerized into predominantly single carbon number synthetic fluids by contacting the oligomers with dimerization catalysts. Preferable dimerization catalysts are, for example, (a) a boron trifluoride and promoter or (b) aluminum chloride. Boron trifluoride can be used as a catalyst in step (c) together with a compound commonly called a promoter or a co-catalyst. The co-catalyst can be any compound which complexes with boron trifluoride to form a coordination compound which is catalytically active for the oligomerization reaction. Included in this list of co-catalysts are aliphatic ethers, such as dimethyl ether, diethyl ether and the like; aliphatic alcohols such as methanol, ethanol, n-butanol, decanol, and the like; polyols such as ethylene glycol, glycerol and the like; water; aliphatic carboxylic acids such as ascetic acid, propanoic acid, butyric acid, and the like; esters, such as ethyl acetate, methyl propionate, and the like; ketones, such as acetone and the like; aldehydes, such as acetaldehyde, benzaldehyde, and the like;

acid anhydrides, such as acetic acid anhydride, succinic anhydride, and the like. It is preferred that the above-described co-catalyst have from one to about 10 carbon atoms although higher carbon co-catalyst compounds can be used. The co-catalyst can be used in a catalytic amount such as from about 0.01 to about 3.0 weight percent of the 1-olefin, preferably from about 0.1 to about 1.0 weight percent. When the amount is low; the reaction becomes slow and when it is too high, there is no added benefit. Examples of useful catalysts and their preparation are described in U.S. Pat. No. 4,045,507 which disclosure is hereby incorporated by reference.

The pressure of boron trifluoride gas that is maintained in step (c) can suitably range from about 5 to about 500 PSIG (0.352 to 35.2 Kg/cm$^2$) or higher with a preferred range of about 50 to about 150 PSIG (3.52 to 10.5 Kg/cm$^2$). Alternatively, the boron trifluoride gas can be bubbled through the liquid into the first stage maintained under atmospheric or higher pressure with boron trifluoride gas recycle. Other procedures are known in the art for introducing boron trifluoride into the reaction solution.

The temperature required for suitable dimerization can broadly range from about −20° to about 90° C. with a temperature in the range of about 20° to about 70° C. being preferred. The higher the temperature the greater the rate of catalyst consumption and the lower the rate of reaction while the lower the temperature, the greater the cooling costs with the reaction rate being satisfactory at the lower temperatures. The reaction is most preferably carried out at a temperature in the range of from about 40° C. to 70° C.

The synthetic fluids can be hydrogenated to provide hydrogenated synthetic fluids (saturated synthetic fluid) that are particularly suitable for motor oil and other lubricating oil applications. Hydrogenation can be carried out by contacting the synthetic fluid product with hydrogen at a temperature in the range from about 100° C. to about 400° C. and a pressure in the range from 100 to 3000 PSIG (7 to 210 Kg/cm$^2$) in the presence of a hydrogenation catalyst.

The unsaturated synthetic hydrocarbon fluid prepared by the method described above can be hydrogenated by a reaction with hydrogen gas in the presence of a catalytic amount (0.1 to 5 wt. %) of a hydrogenation catalyst. Examples of suitable hydrogenation catalysts are metals of Group VIII of the Periodic Table such as iron, cobalt, nickel, rhodium, palladium and platinum. These catalysts may be deposited on alumina, on silica, or on activated carbon in preferred embodiments. Of these catalysts, palladium and nickel are preferred. Palladium on activated carbon and nickel on kieselguhr are especially preferred. In an embodiment of the invention, the synthesized oligomer has some unsaturation. The unsaturation is primarily in the form of vinylidene groups. In another embodiment of the invention the synthesized oligomer is saturated. In an aspect of the invention, the oligomer is synthesized as an unsaturated oligomer, and it is subsequently hydrogenated to produce a saturated oligomer. Examples of useful catalysts are described in U.S. Pat. No. 7,129,197, which disclosure is hereby incorporated by reference.

Hydrogenation can be carried out by contacting the unsaturated hydrocarbon synthetic fluid product with hydrogen at a temperature in the range of from about 100° C., preferably from about 200° C., to about 400° C., preferably to about 350° C. and a pressure in the range of from about 100 psig (7 Kg/cm$^2$) preferably from about 500 psig (35.2 Kg/cm$^2$), to about 3000 psig (210 Kg/cm$^2$), preferably to about 1000 psig (70 Kg/cm$^2$) in the presence of a hydrogenation catalyst.

The synthetic hydrocarbon fluid products obtained by this process are predominantly single carbon number hydrocarbons with low volatility and high oxidative stability as compared to PAO made by other methods and are useful as high performance lubricants.

In one embodiment, the resulting predominantly single carbon synthetic hydrocarbon fluid has a carbon number of 60, a Noack volatility value of less than 1.5 weight percent, preferably 1.2 weight percent (according to ASTM method D6375), an average of about one quaternary carbon atom per molecule (measured by nuclear magnetic resonance spectroscopy) and a boiling point distribution at 10 weight percent distilled to 90 weight percent distilled within the range of 500° C. to 650° C., more preferably in the range of 525° C. to 625° C. (according to ASTM method D6417).

In another embodiment, the resulting predominantly single carbon number synthetic hydrocarbon fluid having a carbon number of 80, a Noack volatility value of less than 1.0 weight percent, preferably 0.7 weight percent (according to ASTM method D5800), a branching of an average of about one quaternary carbon atom per molecule and a boiling point distribution at 10 weight percent distilled to 90 weight percent distilled within the range of 500° C. to 690° C., more preferably in the range of 525° C. to 680° C. (according to ASTM method D2887).

The oxidative stability of the synthetic hydrocarbon fluid should preferably be from about 20 minutes, more preferably from about 25 minutes, to 30 minutes, more preferably 40 minutes as measured by Pressure differential scanning calorimeter (PDSC) minutes to maximum exotherm at 160° C. and 500 psig oxygen.

Decene is used herein to describe one embodiment of the invention. Other alpha olefins can also be used according to the invention. Long chain olefin hydrocarbon oligomers are produced when decene is reacted with a single site catalyst (Shown in Step 1). The olefin oligomers have a reactive double bond. The oligomers are separated into the trimer and tetramer components and then the double bonds can be reacted together dimerizing the separated hydrocarbon oligomers (Shown in Step 2). Dimerizing the oligomers shown in step 1 with 30 and 40 carbon atoms doubles the number of carbon atoms and new synthetic fluids are obtained with 60 and 80 carbon atoms, respectively.

Step (1) $C_{10} \rightarrow C_{20}, C_{30}, C_{40}$, etc.
Step (2) $C_{30}, C_{40} \rightarrow C_{60}, C_{80}$ The two reactions oligomerization followed by dimerization can produce single carbon number synthetic fluids having viscosities at 100° C. of about 12 cSt and about 18 cSt that are not readily available without blending different polyalpha olefins. Commercially available 12 cSt mineral oil typically has a Noack volatility value of 2 weight percent.

The synthetic hydrocarbon fluids made by this invention will have narrower boiling point distributions than mineral oils and currently commercial synthetic fluids because they are single carbon number compounds and contain a narrower distribution of isomers. Synthetic fluids with narrow boiling point distribution will have lower volatility than mineral oils with equivalent viscosities. Low volatility of the synthetic fluids should improve wear properties by adhering to hot metal surfaces longer. The synthetic fluids with about 60 carbon atoms will have outstanding volatility compared to commercially available heavy oils.

Tetradecene is used as another example herein to describe another embodiment of the invention. Again, other alpha olefins can also be made according to the invention. Long chain alphaolefins, hydrocarbon oligomers, are produced when tetradecene is reacted with a single site catalyst (Shown in Step 1B). The oligomers have a reactive double bond at the terminal position. The oligomers are separated into the trimer and tetramer components and then the double bonds can be reacted together dimerizing the oligomers (Shown in Step 2B). Dimerizing long chain olefins (Shown in Step 1B) with 28, 42 and 56 carbon atoms doubles the number of carbon atoms and new synthetic fluids are obtained with 56, 84 and 112 carbon atoms, respectively.

Step (1B) $C_{14} \rightarrow C_{28}, C_{42}, C_{56}$, etc.

Step (2B) $C_{42}, C_{56} \rightarrow C_{84}, C_{112}$, etc.

The two reactions oligomerization followed by dimerization can produce single carbon number synthetic fluid that can produce single carbon number synthetic fluids having higher viscosities than the synthetic fluid produced from 1-decene.

The synthetic hydrocarbon fuel obtained in accordance with embodiments of the invention may be formulated with lubricant oils in amounts from about 0.1 wt % to about 99 wt %. The lubricant oils may also contain a number of conventional additives in amounts required to provide various functions. These additives include, but are not limited to, ashless dispersants, metal or overbased metal detergent additives, anti-wear additives, viscosity index improvers, antioxidants, rust inhibitors, pour point depressants, friction reducing additives, and the like.

Suitable ashless dispersants may include, but are not limited to, polyalkenyl or borated polyalkenyl succinimide where the alkenyl group is derived from a $C_3$-$C_4$ olefin, especially polyisobutenyl having a number average molecular weight of about 5,000 to 7,090. Other well known dispersants include the oil soluble polyol esters of hydrocarbon substituted succinic anhydride, e.g. polyisobutenyl succinic anhydride, and the oil soluble oxazoline and lactone oxazoline dispersants derived from hydrocarbon substituted succinic anhydride and di-substituted amino alcohols. Lubricating oils typically contain about 0.5 to about 5 wt % of ashless dispersant.

Suitable metal detergent additives are known in the art and may include one or more of overbased oil-soluble calcium, magnesium and barium phenates, sulfurized phenates, and sulfonates (especially the sulfonates of $C_{16}$-$C_{50}$ alkyl substituted benzene or toluene sulfonic acids which have a total base number of about 80 to 300). These overbased materials may be used as the sole metal detergent additive or in combination with the same additives in the neutral form; but the overall metal detergent additive should have a basicity as represented by the foregoing total base number. Preferably they are present in amounts of from about 3 to 6 wt % with a mixture of overbased magnesium sulfurized phenate and neutral calcium sulfurized phenate (obtained from $C_9$ or $C_{12}$ alkyl phenols).

Suitable anti-wear additives include, but are not limited to, oil-soluble zinc dihydrocarbyldithiophosphates with a total of at least 5 carbon atoms and are typically used in amounts of about 1-6% by weight.

Suitable viscosity index improvers, or viscosity modifiers, include, but are not limited to olefin polymers, such as polybutene, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post-grafted polymers of ethylene and propylene with an active monomer such as maleic anhydride which may be further reacted with alcohol or an alkylene polyamine, styrene-maleic anhydride polymers post-reacted with alcohols and amines and the like. These are used as required to provide the viscosity range desired in the finished oil in accordance with known formulating techniques.

Examples of suitable oxidation inhibitors include, but are not limited to, hindered phenols, such as 2,6-di-tertiarybutyl-paracresol, amines sulfurized phenols and alkyl phenothiazones. Usually, a lubricating oil may contain about 0.01 to 3 wt % of oxidation inhibitor, depending on its effectiveness. For improved oxidation resistance and odor control, it has been observed that up to about 5 wt % of an antioxidant should be included in the aforementioned formula. One suitable example of such, butylated hydroxytoluene ("BHT"), or di-t-butyl-p-cresol, is sold by many supplies including Rhein Chemie and PMX Specialties. Another suitable example is Irganox L-64 from Ciba Gigy Corp.

Rust inhibitors may be employed in very small proportions such as about 0.1 to 1 weight percent with suitable rust inhibitors being exemplified by $C_9$-$C_{30}$ aliphatic succinic acids or anhydrides such as dodecenyl succinic anhydride. Antifoam agents are typically included, but not limited to polysiloxane silicone polymers present in amounts of about 0.01 to 1 wt %.

Pour point depressants are used generally in amounts of from about 0.01 to about 10.0 wt %, more typically from about 0.1 to about 1 wt %, for most mineral oil basestocks of lubricating viscosity. Illustrative of pour point depressants which are normally used in lubricating oil compositions include, but are not limited to, polymers and copolymers of n-alkyl methacrylate and n-alkyl acrylates, copolymers of di-n-alkyl fumarate and vinyl acetate, alpha-olefin copolymers, alkylated naphthalenes, copolymers or terpolymers of alpha-olefins and styrene and/or alkyl styrene, styrene dialkyl maleic copolymers and the like.

As discussed in U.S. Pat. No. 6,245,719, which is fully incorporated by reference herein, a variety of additives may be used to improve oxidation stability and serviceability of lubricants used in automotive, aviation, and industrial applications. These additives include calcium phenate, magnesium sulfonate and alkenyl succinimide to agglomerate solid impurities, a combination of an ashless dispersant, metallic detergent and the like, an oxidation inhibitor of sulfur-containing phenol derivative or the like, an oxidation inhibitor or the like, or mixtures thereof.

While the invention is amenable to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

EXAMPLES

In all examples, the procedures outlined below were used.
Procedure for Catalyst Preparation:

Dry a 100 ml round bottom flask (with a magnetic stir bar) in an 80° C. oven and flush it with nitrogen gas until it cools down to room temperature via rubber septum. Quickly snaph-the 1 gram catalyst ($Cp_2ZrCl_2$) and transfer it into the flask, then seal the flask with rubber septa. Continue to purge it with nitrogen gas. Add 54 ml of dry toluene to the flask and stir to dissolve the catalyst into solution. Store in Nitrogen atmosphere.

Procedure for Polymerization Reaction

Dry a 3 neck (250 ml) round bottom flask with magnetic stir bar, a condenser, two addition flasks under nitrogen atom.

Charge the reactor with 50 ml of toluene. Charge one of the addition flasks with a mixture of 100 ml of 1-alkene and 20 ml of 3.3 M methylaluminoxane (MAO). Charge the other addition flask with 4 ml metallocene catalyst solution. Drip the solutions from the addition flasks while continuously stirring toluene in the flask. Maintain polymerization temperature at 50-70° C. (preferable at 60° C.) for 1 hour. Stop the reaction by bringing the reactor temperature to ambient and adding 100 ml of 10% hydrochloric acid into the reaction mixture and start mixing. This step is to deactivate the residual MAO. Mix for at least one hour. Isolate the organic layer and wash it three more times with 100 ml of distilled water. Collect the organic layer, dry over $MgSO_4$ and remove toluene solvent. Collect the product. Weigh it and calculate the yield.

Procedure for Dimerization Reaction Using BF3 Gas in Presence of Catalytic Amount of Alcohol:

Dry the reactor with a magnetic stirrer by flushing the unit with Nitrogen gas. Add desired amount of vinylidene hydrocarbon from polymerization reaction. Add catalytic amount of n-butanol. Pressure up (30 psi) and flush the system with Nitrogen one time. Pressure-up the unit with Boron Trifluoride gas (50 psi). Stir the reaction mixture. This reaction is exothermic and a slight increase in the temperature (<10° C.) is expected. Once the reactor temperature stabilizes, add heat to maintain 40-45° C., continue stirring till BF3 absorption stops. Generally, reaction is complete by 3-6 hours. Vent the excess BF3 gas via caustic scrubber very slowly. Most of the gas is absorbed in the scrubber. Flush one time with nitrogen gas and quench the reaction by adding 10% KOH solution in water. Let the reaction mixture stir for 30 minute. Separate the organic layer and wash with water (3 times). Analyze the product.

Procedures for Hydrogenation Reaction:

Charge the reactor vessel with predetermined amount of dimerization product that needs to be hydrogenated. Add desired amount of heptane solvent to the vessel. Weigh desired amount of hydrogenation catalyst (e.g. 10 wt % palladium on activated carbon and typically the ratio between palladium and polymerization product is 1%). Add it to the polymerization product/heptane mixture in the reactor vessel. Assemble the vessel to the reactor stand and seal the reactor. Slightly charge the reactor with hydrogen gas. Purge the reactor three times to remove any residual air inside the reactor. Turn on the mixer and set the speed at 2000 RPM. Charge the reactor with about 500 psig of hydrogen gas and start heating. After the temperature reaches 200° C., further charge hydrogen gas into the reactor to reach 900 psig of pressure. Let the hydrogenation reaction run overnight. To stop the reaction, turn off the heating and mixing. Slowly open the vent valve to release the pressure inside reactor to ambient. Purge the reactor three times with nitrogen gas to remove residual hydrogen gas from the reactor. Make sure the reactor is at ambient temperature and pressure. Dissemble the reactor and transfer the hydrogenation reaction mixture into a desired container. Filter the reaction mixture to remove the solid catalyst. Collect the clear solution. Rotary evaporation of the solution to remove heptane solvent yielded the product.

Hydrogenation Procedure Using a Continuous Unit:

The olefin was used as a feed in a pilot scale hydrotreating unit using a typical lube oil hydrotreating catalyst (Ni—Mo or Ni—Mo—Co, etc.) at a space velocity of 0.5 per hour, at 680 of and at 2000 psi hydrogen pressure. The unit was allowed to line-out for 9 hours before collecting the sample. The properties of the product are tabulated in the table.

Comparative Example 1

Preparation of 2-Octyl-1-dodecene [C10H23-C(C8H17)=CH2]: A 3 neck (250 ml) round bottom flask with magnetic stir bar, a condenser and other glassware were dried in the oven for at least 8 hours. All glassware from the oven was removed and quickly assembled. Nitrogen purge was started immediately and continued. The flask was then charged with 50 ml of toluene and 100 ml of 1-decene. It was heated and maintained at 60° C. temperature. 20 ml of 3.3M MAO was added using a syringe with stirring and continued stirring for 20 min. The catalyst $(iPrCp)_2ZrCl_2$ (4 ml) (see preparation of catalyst above) was added via a syringe and stirred for 1 hour at 60° C. (range 50-70° C.). The catalyst was deactivated by adding 100 ml of 10% hydrochloric acid into the reaction mixture and stiffing for 1 hour. The organic layer of the mixture was isolated and washed three times with 100 ml distilled water. The organic layer was collected, toluene was removed and the product was fractionated into various viscosity grade fluids by vacuum distillation. The total product yield was 58.24 g (83.2%). The $C_{20}$ vinylidene product was collected at 83-137° C. (mostly at 115-118° C.) at 0.05-0.1 mmHg (83.8%) and the residue was $C_{30}$+ (yield 16.2%). Simulated Distillation of $C_{20}$ vinylidene (ASTM D2887): IBP(% W) 521 (° F.); 5% 621; 10% 633; 20% 637; 50% 641; 90% 644; 95% 644; FBP 732.

A reactor with a magnetic stirrer was dried and purged with Nitrogen gas. 401 g of the $C_{20}$ vinylidene hydrocarbon obtained above and 8 ml of n-butanol was then added. The reactor was brought to a pressure of 30 psi and purged with Nitrogen. Boron Trifluoride gas was then introduced and brought to a pressure of 50 psi. The reaction mixture was stirred for 6 hours. This reaction is exothermic and a slight increase in the temperature (<10° C.) was observed. Once the reactor temperature was stabilized, it was heated to maintain 40-45° C., continued stirring till BF3 absorption stops. The excess BF3 gas was then vented via caustic scrubber very slowly. Most of the gas is absorbed in the scrubber. Reactor was flushed one time with nitrogen gas and quenched the reaction by adding 10% KOH solution in water. The reaction mixture was further stirred for 30 minute. Organic layer was separated, and wash with water (3 times). Simulated distillation (ASTM D6417) analysis showed 70% of $C_{40}$ molecule and 30% of $C_{20}$ molecule. This mixture of $C_{20}$ and $C_{40}$ was hydrogenated using typical hydrogenation conditions described, followed by vacuum distillation. Properties of $C_{40}$ molecule is given in Comparative Example 1, Table 1. Cold Cranking Viscosity of $C_{40}$ molecule at −25° C. and at −30° C. was 2880 cP and 4810 cP respectively. Similarly, Brookfield viscosity of C40 molecule at −25 C, −30° C., −35° C. and at −40° C. was 3225, 5200, 8870 and 17450 cP respectively.

Example 1

The 1-decene (3 gallons) was processed in the continuous laboratory reactor. Experimental procedure was same as Comparative Experiment 1, except that 1-decene, MAO in toluene, and metallocene catalyst in toluene was continuously fed into a pressure reactor through independent channels with a residence time of 60 min in the reactor. The Zr/Olefin target was 1 mol/kmol, but varied from 0.3 to 3 mol/kmol. The Al/Zr target was 200 mol/mol, but varied from 100 to 400 mol/mol, during the entire experiment period.

The first gallon batch of product was worked up using acid wash followed by water wash, but separation of the organic phase and aqueous phase was difficult. Also, this method produced a lot of waste aqueous phase. It was found that if about 5% water is added to the reaction product (instead of 100% dilute acid followed by 100% water), the MAO is completely decomposed and separates as a solid phase instead of aqueous slurry. The solid phase is easily filtered out. This method was used for the remainder of the reaction product. The deactivated reaction product was rotary evaporated to remove toluene and decene (discarded), and then vacuum distilled into fractions. There was 3330 g (31%) unreacted decene, 4521 g (42%) of $C_{20}$ Vinylidene, 1403 g (13%) of $C_{30}$ Vinylidene, 507 g of $C_{40}$ vinylidene, and 979 g of $C_{50+}$ Vinylidene. The distillation was monitored by simulated distillation (ASTM D6417).

Separated $C_{30}$ Vinylidene prepared above was used for BF3 reaction (see general procedure above). Dimerization reaction from $C_{30}$ to $C_{60}$ went only to 10% when the reaction was carried out at 40-45° C., under 50 psig $BF_3$ pressure.

$C_{30}$ Vinylidene (400 g) was then treated with $BF_3$, with catalytic amount of n-butanol (8 ml, 2 wt. %) at 55-65° C., under 60-65 psig pressure for 30 hours. Conversion to $C_{60}$ was 59% with this reaction condition. Dimerization work-up was as in the procedure for dimeerization, followed by hydrogenation according to the procedure described above and vacuum distillation yielded $C_{30}$ (41%) and $C_{60}$ (59%) [Example 1, Table 1].

Example 2

The reactor with a magnetic stirrer was dried and flushed the unit with Nitrogen gas. 316 g $C_{40}$ vinylidene (as prepared in Example 1) and catalytic amount of n-butanol (5.4 ml) was then added. The reactor was further pressured-up (30 psi) and flush the system with Nitrogen one time. Boron Trifluoride gas was then introduced and pressured-up (65 psig). Reaction mixture was stirred for 1 hour. This reaction is exothermic and a slight increase in the temperature (<10° C.) was observed. Once the reactor temperature was stabilized, it was heated to maintain 55-65° C., continued stirring till $BF_3$ absorption stops (36 hours). The excess $BF_3$ gas was then vented via caustic scrubber very slowly. Most of the gas is absorbed in the scrubber. Reactor was flushed one time with nitrogen gas and quenched the reaction by adding 10% KOH solution in water. The reaction mixture was further stirred for 30 minute. Organic layer was separated, and wash with water (3 times). Simulated distillation (ASTM D6417) analysis showed 68.4% of $C_{80}$ molecule and 31.6% of $C_{40}$ molecule. This mixture of $C_{40}$ and $C_{80}$ was hydrogenated at 210-215° C., 1000-1100 psig hydrogen pressure with 5% Pd/C (8.02 g) for 48 hours. This was followed by vacuum distillation. The fraction collected at 230-250° C. at 0.06-0.08 mmHg was $C_{40}$ molecule and the residue in the flask identified as $C_{80}$ molecule. Properties of $C_{40}$ molecule is similar to Comparative Example 1, Table 1. Properties of $C_{80}$ molecule is given in Example 2, Table 1.

TABLE 1

Properties of Examples and Comparative Example

| Property | ASTM Method | Comparative Example 1 | Example 1 | Example 2 |
|---|---|---|---|---|
| Kin. Vis, cSt at 40 C. | D445 | 47 | 93 | 152 |
| Kin. Vis, cSt at 100 C. | D445 | 7.7 | 12.7 | 17.8 |
| Viscosity Index | D2270 | 131 | 135 | 130 |
| Cloud Point, C. | D5771 | <−69 | <−73 | |
| Pour Point, C. | D5950 | −57 | −54 | |
| PDSC min to max exotherm at 160° C., 500 PSI $O^2$ | D6186 | 33 | 25 | 27 |
| TGA Noack wt % | D6375 | 1.9 | 1.2 | 0.7 |
| Bromine Index | D2710 | <100 | <100 | 155 |
| Sim. Dist., C. | D6417 | | | |
| 10 wt % off | | 479 | 528 | 520 |
| 50 wt % off | | 496 | 572 | 604 |
| 90 wt % off | | 562 | 620 | 669 |

Motor Oil Examples 1-12

Figure 2:
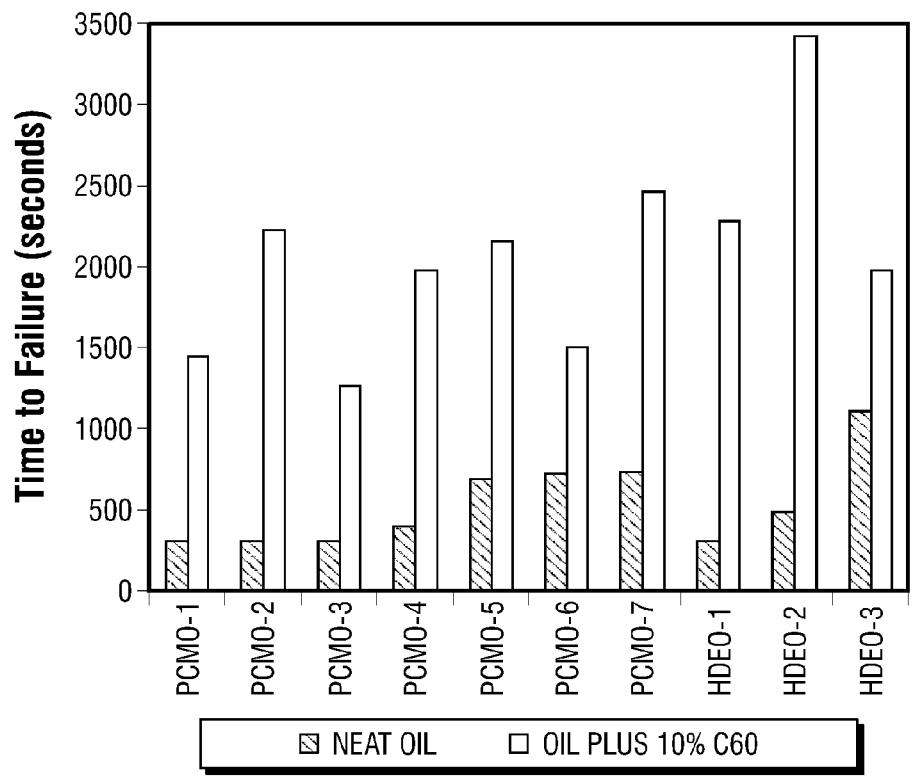
FIG. 2 is a plot of performance data of commercial lubricants with and without addition of the PAO made according to the invention, using an Optimal instrument to measure wear rate of a lubricated surface.

Twelve commercial motor oils were modified by addition of 10% by weight of $C_{60}$ synthetic hydrocarbon made from 1-decene from Example 1 and tested using a High Temperature Optimal Test. Seven different commercially available 5W30 GF-4 Passenger car Motor Oils (PCMO) from various manufacturers and three different commercially available 15W40 CI-4 Plus Heavy duty Engine Oils (HDEO) from various manufacturers were used. The time to failure was taken as the time at which there was a sharp increase in friction coefficient, typically to a value of 0.4. The time to failure increased by a factor of 2 to 8 when the example 1 synthetic hydrocarbon was added to the commercial oils, indicating a significant improvement in resistance to scuffing. The High Temperature Optimal Data is shown in FIG. 2. FIG. 2 is a high temperature optimol test using commercial PCMOs and HDEOs top treated with 10% by weight of the synthetic hydrocarbon fluid from Example 1. Test conditions were 100 Newton load, 50 Hz, 280° C., 12 ul samples of the following oils. The results shown in the following table are time to failure in the unit of seconds.

TABLE 2

High Temperature Optimol Testing

| Commercial Motor Oil | neat | 10% $C_{60}$ | types | API Service Category |
|---|---|---|---|---|
| PCMO-1 | 300 | 1440 | 5W30 | GF-4 |
| PCMO-2 | 300 | 2220 | 5W30 | GF-4 |
| PCMO-3 | 300 | 1260 | 5W30 | GF-4 |
| PCMO-4 | 400 | 1980 | 5W30 | GF-4 |
| PCMO-5 | 690 | 2160 | 5W30 | GF-4 |
| PCMO-6 | 720 | 1500 | 5W30 | GF-4 |

TABLE 2-continued

High Temperature Optimol Testing

| Commercial Motor Oil | neat | 10% C$_{60}$ | types | API Service Category |
|---|---|---|---|---|
| PCMO-7 | 730 | 2460 | 5W30 | GF-4 |
| HDEO-1 | 300 | 2280 | 15W40 | CI-4 Plus |
| HDEO-2 | 480 | 3420 | 15W40 | CI-4 Plus |
| HDEO-3 | 1110 | 1980 | 15W40 | CI-4 Plus |

We claim:

1. A process for the preparation of a synthetic predominantly single carbon number hydrocarbon fluid comprising the steps of:
    (a) contacting an alpha olefin having a carbon number of 4 to 30 with a single site catalyst under conditions effective to produce reactive hydrocarbon oligomers that contain reactive double bonds and comprising predominantly dimers, trimers, and tetramers, wherein at least 10 weight percent of such reactive hydrocarbon oligomers is at least one of trimers and tetramers;
    (b) separating at least one of said trimers and tetramers in said reactive hydrocarbon oligomers;
    (c) dimerizing said separated at least one of said trimers and tetramers by contacting said separated at least one of said trimers and tetramers with a dimerization catalyst thereby producing an unsaturated synthetic hydrocarbon fluid; and
    (d) contacting said unsaturated synthetic hydrocarbon fluid with hydrogen in the presence of a hydrogenation catalyst thereby producing a synthetic hydrocarbon fluid having predominantly single carbon number.

2. The process of claim 1 wherein the alpha olefin is selected from the group consisting of 1-butene, 1-pentene, 1-hexene, 1-heptene, 1-octene, 1-nonene, 1-decene, 1-dodecene, 1-tetradecene, 1-hexadecene, 1-octadecene, 1-eicosene, 4-ethyl-1-pentene, 2-methyl-1-hexene, and 4-methyl-1-pentene.

3. The process of claim 2 wherein the alpha olefin is selected from 1-octene, 1-decene, 1-dodecene and 1-tetradecene.

4. The process of claim 2 wherein the single site catalyst comprises a catalyst selected from the group consisting of organometallic complexes containing zirconium, titanium, niobium, and hafnium.

5. The process of claim 4 wherein the single site catalyst is a complex of bis(cyclopentadienyl)zirconium dichloride and an alkylaluminoxane.

6. The process of claim 2 wherein step (a) is carried out at a temperature within the range of about 0° C. to about 90° C.

7. The process of claim 2 wherein dimerization catalyst is selected from the group consisting of (a) a boron trifluoride and a co-catalyst and (b) aluminum chloride.

8. The process of claim 7 wherein step (c) is carried out at a temperature in the range of about −20° C. to about 90° C.

9. The process of claim 7 wherein step (c) is carried out at a temperature in the range of about 20° C. to about 70° C.

10. The process of claim 1 wherein said at least one of trimers and tetramers consists of trimers.

11. The process of claim 10 wherein step (a) is carried out at a temperature in the range of about 20° C. to about 60° C.

12. A predominantly single carbon number synthetic hydrocarbon fluid having a carbon number of 60, a Noack volatility value of less than 1.5 weight percent, an average of about one quaternary carbon atom per molecule and a boiling point distribution at 10 weight percent distilled to 90 weight percent distilled within the range of 500° C. to 650° C.

13. The predominantly single carbon number synthetic hydrocarbon fluid of claim 12 having a viscosity at 100° C. of about 12 cSt.

14. A predominantly single carbon synthetic hydrocarbon fluid having a carbon number of 80, a Noack volatility value of less than 1.0 weight percent, an average of about one quaternary carbon atom per molecule and a boiling point distribution at 10 weight percent distilled to 90 weight percent distilled within the range of 500° C. to 690° C.

15. The predominantly single carbon number synthetic hydrocarbon fluid of claim 14 having a viscosity at 100° C. of about 18 cSt.

16. A predominantly single carbon number synthetic hydrocarbon fluid comprising a major amount of a compound having the formula:

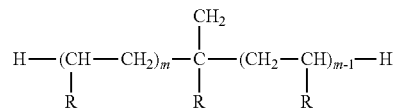

wherein m is an integer from 2 to 4 and R is an alkyl group having a carbon number of 2 to 28.

17. A predominantly single carbon number synthetic hydrocarbon fluid comprising a major amount of a compound having the formula:

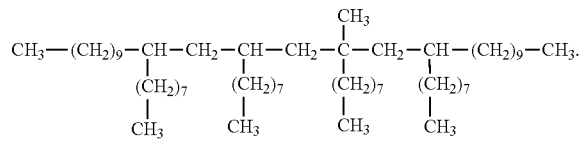

18. A predominantly single carbon synthetic hydrocarbon fluid comprising a major amount of a compound having the formula:

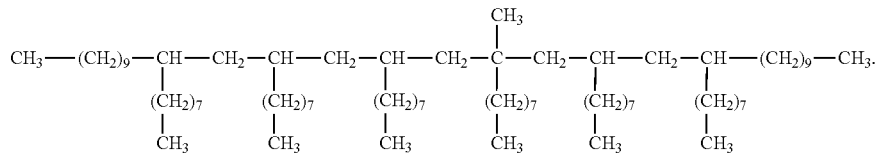

19. The predominantly single carbon number synthetic hydrocarbon fluid produced by the process of claim 1.

20. A lubricating composition comprising predominantly single carbon number synthetic hydrocarbon fluid produced by the process of claim 1.

* * * * *